United States Patent
Tran et al.

(10) Patent No.: US 11,103,262 B2
(45) Date of Patent: Aug. 31, 2021

(54) BALLOON-BASED INTRAVASCULAR ULTRASOUND SYSTEM FOR TREATMENT OF VASCULAR LESIONS

(71) Applicant: Boston Scientific Scimed, Inc., Maple Grove, MN (US)

(72) Inventors: Binh C. Tran, Minneapolis, MN (US); Douglas Dean Pagoria, Evergreen, CO (US); Roger W. McGowan, Otsego, MN (US); Christopher Smuk, Champlin, MN (US); Daniel Frank Massimini, Brooklyn Park, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 160 days.

(21) Appl. No.: 16/351,183

(22) Filed: Mar. 12, 2019

(65) Prior Publication Data
US 2019/0282249 A1     Sep. 19, 2019

Related U.S. Application Data

(60) Provisional application No. 62/642,830, filed on Mar. 14, 2018.

(51) Int. Cl.
*A61B 17/22*     (2006.01)
*A61B 17/00*     (2006.01)
(Continued)

(52) U.S. Cl.
CPC .............................. *A61B 17/2202* (2013.01); *A61B 2017/00938* (2013.01); *A61B 2017/00942* (2013.01);
(Continued)

(58) Field of Classification Search
CPC .............. A61B 17/22; A61B 17/22012; A61B 17/22022; A61B 17/221; A61B 17/2202;
(Continued)

(56) References Cited

U.S. PATENT DOCUMENTS

| | | | |
|---|---|---|---|
| 4,955,895 A | * | 9/1990 | Sugiyama ............ A61M 25/104 604/103.1 |
| 5,372,138 A | | 12/1994 | Crowley et al. |

(Continued)

FOREIGN PATENT DOCUMENTS

| | | |
|---|---|---|
| CN | 102057422 | 5/2011 |
| CN | 109223100 | 1/2019 |

(Continued)

OTHER PUBLICATIONS

"International Search Report and Written Opinion," for PCT Application No. PCT/2019/022016 dated May 29, 2019 (16 pages).

(Continued)

*Primary Examiner* — Vi X Nguyen
(74) *Attorney, Agent, or Firm* — Roeder & Broder LLP; James P. Broder

(57) ABSTRACT

An ultrasound catheter may be adapted for placement within a blood vessel having a vessel wall for treating a vascular lesion within or adjacent the vessel wall. The ultrasound catheter includes an elongate shaft extending from a distal region to a proximal region and an ultrasound transducer that is disposed relative to the distal region of the elongate shaft and is adapted to impart near-field acoustic pressure waves upon the vascular lesion in order to mechanically modify the vascular lesion. An inflatable balloon is disposed about the ultrasound transducer and is coupled to the elongate shaft, the inflatable balloon having a collapsed configuration suitable for advancing the ultrasound catheter through a patient's vasculature and an expanded configuration suitable for anchoring the ultrasound catheter in position relative to a treatment site.

20 Claims, 5 Drawing Sheets

(51) Int. Cl.
*A61M 25/10* (2013.01)
*A61M 37/00* (2006.01)

(52) U.S. Cl.
CPC .......... *A61B 2017/22028* (2013.01); *A61B 2017/22054* (2013.01); *A61B 2017/22062* (2013.01); *A61B 2017/22069* (2013.01); *A61M 25/1011* (2013.01); *A61M 37/0092* (2013.01); *A61M 2025/1075* (2013.01); *A61M 2025/1088* (2013.01); *A61M 2025/1093* (2013.01)

(58) Field of Classification Search
CPC .......... A61B 2017/00942; A61B 2017/22069; A61B 2017/22062; A61B 2017/22028; A61B 2017/00938
See application file for complete search history.

(56) References Cited

U.S. PATENT DOCUMENTS

| | | |
|---|---|---|
| 5,609,606 A | 3/1997 | O'Boyle |
| 5,611,807 A | 3/1997 | O'Boyle |
| 5,772,609 A | 6/1998 | Nguyen et al. |
| 6,080,119 A | 6/2000 | Schwarze et al. |
| 6,123,923 A | 9/2000 | Unger |
| 6,139,510 A | 10/2000 | Palermo |
| 6,186,963 B1 | 2/2001 | Schwarze et al. |
| 6,210,404 B1 | 4/2001 | Shadduck |
| 6,514,203 B2 | 2/2003 | Bukshpan |
| 6,524,251 B2 | 2/2003 | Rabiner et al. |
| 6,607,502 B1 | 8/2003 | Maguire et al. |
| 6,652,547 B2 | 11/2003 | Rabiner et al. |
| 6,849,994 B1 | 2/2005 | White et al. |
| 7,470,240 B2 | 12/2008 | Schultheiss et al. |
| 7,810,395 B2 | 10/2010 | Zhou |
| 7,867,178 B2 | 1/2011 | Simnacher |
| 7,985,189 B1 | 7/2011 | Ogden et al. |
| 8,162,859 B2 | 4/2012 | Schultheiss et al. |
| 8,166,825 B2 | 5/2012 | Zhou |
| 8,556,813 B2 | 10/2013 | Cashman et al. |
| 8,574,247 B2 | 11/2013 | Adams et al. |
| 8,709,075 B2 | 4/2014 | Adams et al. |
| 8,728,091 B2 | 5/2014 | Hakala et al. |
| 8,747,416 B2 | 6/2014 | Hakala et al. |
| 8,888,788 B2 | 11/2014 | Hakala et al. |
| 8,956,371 B2 | 2/2015 | Hawkins et al. |
| 8,956,374 B2 | 2/2015 | Hawkins et al. |
| 9,005,216 B2 | 4/2015 | Hakala et al. |
| 9,011,462 B2 | 4/2015 | Adams et al. |
| 9,011,463 B2 | 4/2015 | Adams et al. |
| 9,044,619 B2 | 6/2015 | Hawkins et al. |
| 9,072,534 B2 | 7/2015 | Adams et al. |
| 9,131,949 B2 | 9/2015 | Coleman et al. |
| 9,138,249 B2 | 9/2015 | Adams et al. |
| 9,180,280 B2 | 11/2015 | Hawkins et al. |
| 9,220,521 B2 | 12/2015 | Hawkins et al. |
| 9,237,984 B2 | 1/2016 | Hawkins et al. |
| 9,289,224 B2 | 3/2016 | Adams et al. |
| 9,320,530 B2 | 4/2016 | Grace |
| 9,333,000 B2 | 5/2016 | Hakala et al. |
| 9,375,223 B2 | 6/2016 | Wallace |
| 9,433,428 B2 | 9/2016 | Hakala et al. |
| 9,510,887 B2 | 12/2016 | Burnett |
| 9,554,815 B2 | 1/2017 | Adams |
| 9,555,267 B2 | 1/2017 | Ein-gal |
| 9,566,209 B2 | 2/2017 | Katragadda et al. |
| 9,579,114 B2 | 2/2017 | Mantell et al. |
| 9,642,673 B2 | 5/2017 | Adams et al. |
| 9,730,715 B2 | 8/2017 | Adams |
| 9,814,476 B2 | 11/2017 | Adams et al. |
| 9,861,377 B2 | 1/2018 | Mantell |
| 9,867,629 B2 | 1/2018 | Hawkins |
| 9,955,946 B2 | 5/2018 | Miller et al. |
| 9,993,292 B2 | 6/2018 | Adams et al. |
| 10,039,561 B2 | 8/2018 | Adams et al. |
| 10,159,505 B2 | 12/2018 | Hakala et al. |
| 10,201,387 B2 | 2/2019 | Grace et al. |
| 10,842,567 B2 | 11/2020 | Grace et al. |
| 2003/0176873 A1 | 9/2003 | Chernenko et al. |
| 2004/0002677 A1 | 1/2004 | Gentsler |
| 2004/0097996 A1 | 5/2004 | Rabiner et al. |
| 2004/0162508 A1 | 8/2004 | Uebelacker |
| 2004/0249401 A1 | 12/2004 | Rabiner et al. |
| 2005/0113722 A1 | 5/2005 | Schultheiss |
| 2005/0171527 A1 | 8/2005 | Bhola |
| 2006/0190022 A1 | 8/2006 | Beyar et al. |
| 2006/0241524 A1 | 10/2006 | Lee et al. |
| 2007/0060990 A1 | 3/2007 | Satake |
| 2007/0088380 A1 | 4/2007 | Hirszowicz et al. |
| 2007/0118057 A1 | 5/2007 | Ein-gal |
| 2007/0255270 A1 | 11/2007 | Carney |
| 2007/0270897 A1 | 11/2007 | Skerven |
| 2008/0097251 A1 | 4/2008 | Babaev |
| 2008/0132810 A1 | 6/2008 | Scoseria et al. |
| 2008/0229837 A1 | 9/2008 | Zhou |
| 2008/0296152 A1 | 12/2008 | Voss |
| 2008/0319356 A1 | 12/2008 | Cain et al. |
| 2009/0036803 A1 | 2/2009 | Warlick et al. |
| 2009/0043300 A1 | 2/2009 | Reitmajer et al. |
| 2009/0247945 A1 | 10/2009 | Levit |
| 2010/0016862 A1 | 1/2010 | Hawkins et al. |
| 2010/0036294 A1 | 2/2010 | Mantell et al. |
| 2010/0114020 A1 | 5/2010 | Hawkins et al. |
| 2010/0114065 A1 | 5/2010 | Hawkins |
| 2010/0198114 A1 | 8/2010 | Novak et al. |
| 2010/0199773 A1 | 8/2010 | Zhou |
| 2010/0222786 A1 | 9/2010 | Kassab |
| 2010/0256535 A1 | 10/2010 | Novak et al. |
| 2011/0082534 A1* | 4/2011 | Wallace ............ A61M 37/0092 623/1.11 |
| 2011/0144502 A1 | 6/2011 | Zhou et al. |
| 2011/0208185 A1 | 8/2011 | Diamant et al. |
| 2011/0245740 A1 | 10/2011 | Novak et al. |
| 2012/0071889 A1 | 3/2012 | Mantell et al. |
| 2012/0095335 A1 | 4/2012 | Sverdlik et al. |
| 2012/0116289 A1 | 5/2012 | Hawkins et al. |
| 2012/0157892 A1 | 6/2012 | Reitmajer et al. |
| 2012/0203255 A1 | 8/2012 | Hawkins et al. |
| 2012/0221013 A1 | 8/2012 | Hawkins et al. |
| 2013/0030431 A1 | 1/2013 | Adams |
| 2013/0030447 A1 | 1/2013 | Adams |
| 2013/0046207 A1 | 2/2013 | Capelli |
| 2013/0218054 A1 | 8/2013 | Sverdlik et al. |
| 2013/0253466 A1 | 9/2013 | Campbell |
| 2013/0345617 A1 | 12/2013 | Wallace |
| 2014/0039513 A1 | 2/2014 | Hakala |
| 2014/0052146 A1 | 2/2014 | Curtis et al. |
| 2014/0052147 A1 | 2/2014 | Hakala et al. |
| 2014/0058294 A1* | 2/2014 | Gross ................... A61B 8/445 601/2 |
| 2014/0257144 A1 | 9/2014 | Capelli et al. |
| 2014/0257148 A1 | 9/2014 | Jie |
| 2014/0276573 A1 | 9/2014 | Miesel |
| 2014/0288570 A1 | 9/2014 | Adams |
| 2015/0359432 A1 | 12/2015 | Ehrenreich |
| 2016/0008016 A1 | 1/2016 | Cioanta et al. |
| 2016/0095610 A1 | 4/2016 | Lipowski et al. |
| 2016/0135828 A1 | 5/2016 | Hawkins et al. |
| 2016/0183957 A1 | 6/2016 | Hakala et al. |
| 2016/0184570 A1 | 6/2016 | Grace et al. |
| 2016/0270806 A1 | 9/2016 | Wallace |
| 2016/0324534 A1 | 11/2016 | Hawkins et al. |
| 2016/0331389 A1 | 11/2016 | Hakala et al. |
| 2016/0367274 A1 | 12/2016 | Wallace |
| 2016/0367275 A1 | 12/2016 | Wallace |
| 2017/0049463 A1 | 2/2017 | Popovic et al. |
| 2017/0056035 A1 | 3/2017 | Adams |
| 2017/0119470 A1 | 5/2017 | Diamant et al. |
| 2017/0135709 A1 | 5/2017 | Nguyen et al. |
| 2017/0303946 A1 | 10/2017 | Ku et al. |
| 2017/0311965 A1 | 11/2017 | Adams |
| 2018/0098779 A1 | 4/2018 | Betelia et al. |
| 2018/0153568 A1 | 6/2018 | Kat-kuoy |
| 2018/0256250 A1 | 9/2018 | Adams et al. |

(56) References Cited

U.S. PATENT DOCUMENTS

| | | |
|---|---|---|
| 2018/0280005 A1 | 10/2018 | Parmentier |
| 2018/0303501 A1 | 10/2018 | Hawkins |
| 2018/0360482 A1 | 12/2018 | Nguyen |

FOREIGN PATENT DOCUMENTS

| | | |
|---|---|---|
| DE | 202008016760 | 3/2009 |
| DE | 102007046902 | 4/2009 |
| DE | 102008034702 | 1/2010 |
| DE | 102009007129 | 8/2010 |
| DE | 202010009899 | 11/2010 |
| DE | 102013201928 | 8/2014 |
| EP | 1179993 | 2/2002 |
| EP | 2157569 | 2/2010 |
| EP | 2879595 | 6/2015 |
| EP | 3318204 | 5/2018 |
| KR | 20050098932 | 10/2005 |
| KR | 20080040111 | 5/2008 |
| WO | 0067648 | 11/2000 |
| WO | 2009121017 | 10/2009 |
| WO | 2012025833 | 3/2012 |
| WO | WO20120052924 A1 | 4/2012 |
| WO | WO20120120495 A2 | 9/2012 |
| WO | 2013119662 | 8/2013 |
| WO | 2016109739 | 7/2016 |
| WO | 2018083666 | 5/2018 |

OTHER PUBLICATIONS

"International Search Report and Written Opinion," for PCT Application No. PCT/US2019/022009 dated May 22, 2019 (14 pages).
International Preliminary Report on Patentability dated Sep. 15, 2020 in PCT Application Serial No. PCT/US2019/022009.

* cited by examiner

BALLOON-BASED INTRAVASCULAR ULTRASOUND SYSTEM FOR TREATMENT OF VASCULAR LESIONS

This application claims the benefit of U.S. Provisional Application No. 62/642,830, filed Mar. 14, 2018, the content of which is herein incorporated by reference in its entirety. This application is co-owned by the owners of U.S. Provisional Application No. 62/642,822, filed Mar. 14, 2018, the content of which is herein incorporated by reference in its entirety.

TECHNICAL FIELD

The present disclosure pertains to medical devices, and methods for manufacturing and using medical devices. More particularly, the disclosure is directed to devices and methods for softening lesions within or near a vascular lumen.

BACKGROUND

Many patients suffer from occluded arteries and other blood vessels which restrict blood flow. Occlusions can be partial occlusions that reduce blood flow through the occluded portion of a blood vessel or total occlusions (e.g., chronic total occlusions) that substantially block blood flow through the occluded blood vessel. In some cases, an occlusion may be or otherwise include a calcified lesion that may impact a physician's ability to place a stent, or conduct balloon angioplasty, for example. The calcified lesion may be treated to soften and weaken the calcified lesion, which can make subsequent treatments such as stenting and balloon angioplasty more effective. A need remains for alternate devices and methods for treating calcified lesions.

SUMMARY

This disclosure provides design, material, manufacturing method, and use alternatives for medical devices. For example, the disclosure is directed to an ultrasound catheter that is adapted for placement within a blood vessel having a vessel wall for treating a calcified lesion within or adjacent the vessel wall The ultrasound catheter includes an elongate shaft extending from a distal region to a proximal region, an ultrasound transducer that is disposed relative to the distal region of the elongate shaft and is adapted to impart near-field acoustic pressure waves within the calcified lesion in order to induce fractures in the calcified lesion. An inflatable balloon is disposed about the ultrasound transducer and is coupled to the elongate shaft, the inflatable balloon having a collapsed configuration suitable for advancing the ultrasound catheter through a patient's vasculature and an expanded configuration suitable for anchoring the ultrasound catheter in position relative to a treatment site.

Alternatively or additionally, the inflatable balloon may include a proximal waist and a distal waist, the inflatable balloon secured to the elongate shaft via the proximal waist and the distal waist, with the proximal waist disposed proximal of the ultrasound transducer and the distal waist disposed distal of the ultrasound transducer.

Alternatively or additionally, the inflatable balloon may be configured to be inflated using an inflation fluid, the inflation fluid being a medium through which the ultrasound transducer transmits acoustic pressure waves.

Alternatively or additionally, the inflation fluid may include pre-formed gas bubbles, droplets or other cavitation nuclei that can be excited into resonance, collapse or other cavitation behavior to generate or amplify the acoustic pressure waves impinging upon the calcified lesion.

Alternatively or additionally, the inflation fluid may include gas bubbles or droplets having an average diameter of about 1 micron to about 2500 microns.

Alternatively or additionally, the inflatable balloon may have an inner surface, and the inner surface of the balloon may include a hydrophilic or hydrophobic treatment.

Alternatively or additionally, a portion of the ultrasound transducer may include a hydrophilic or hydrophobic treatment.

Alternatively or additionally, the inflatable balloon may include an inner surface, and the inner surface of the balloon may include a mechanical or chemical treatment that localizes, traps, collects or nucleates bubbles.

Alternatively or additionally, the inflatable balloon may be a single wall balloon.

Alternatively or additionally, the inflatable balloon may be a double wall balloon, the double wall forming an inner chamber proximate the ultrasound transducer and an outer chamber surrounding the inner chamber.

Alternatively or additionally, the double wall balloon may include an inner wall that is formed of a semipermeable material and an outer wall that is formed of a non-permeable material.

Alternatively or additionally, the ultrasound transducer may be configured to transmit a substantially uniform acoustic pressure over a length of about 10 millimeters to about 60 millimeters at a radial distance of about 1 millimeters to about 8 millimeters as measured from a longitudinal central axis of the elongate shaft.

Alternatively or additionally, the ultrasound transducer may include a plurality of individual ultrasound transducers.

Alternatively or additionally, each of the individual ultrasound transducers may be independently electrically driven.

Another example of the disclosure is an ultrasound device that is adapted for placement within a blood vessel having a vessel wall for causing mechanical fractures in a calcified lesion within or adjacent the vessel wall. The ultrasound device includes an elongate shaft extending from a distal region to a proximal region and an ultrasound transducer that is disposed within the distal region of the elongate shaft and is ultrasound transducer adapted to impart unfocused acoustic pressure waves upon the calcified lesion in order to induce fractures in the calcified lesion. An inflatable balloon is disposed about the ultrasound transducer and coupled to the elongate shaft. The ultrasound transducer has an effective length that is at least twice a distance between the ultrasound transducer and the calcified lesion when the ultrasound device is disposed proximate the calcified lesion.

Alternatively or additionally, the inflatable balloon may include a proximal waist and a distal waist, the inflatable balloon secured to the elongate shaft via the proximal waist and the distal waist, with the proximal waist disposed proximal of the ultrasound transducer and the distal waist disposed distal of the ultrasound transducer.

Another example of the disclosure is a method of treating a calcified lesion that is within or proximate a vessel wall forming part of a blood vessel. An ultrasound catheter is advanced through a patient's vasculature until reaching a desired treatment site proximate the calcified lesion, the ultrasound catheter including an ultrasound transducer secured relative to an inner shaft and an inflatable balloon secured to the inner shaft and disposed about the ultrasound transducer. The inflatable balloon is inflated with an inflation fluid to secure the ultrasound catheter in position proximate the calcified lesion. The ultrasound transducer is driven to produce near-field acoustic pressure waves within a thickness of the vessel wall and the calcified lesion in order to induce fractures within the calcified lesion. The inflatable balloon is deflated to permit repositioning or removal of the ultrasound catheter.

Alternatively or additionally, inflating the inflatable balloon with inflation fluid may include inflating the inflatable balloon with an inflation fluid that includes cavitation nuclei having an average diameter of about 1 micron to about 2500 microns.

Alternatively or additionally, the inflatable balloon may include an inner chamber and an outer chamber, and inflating the inflatable balloon with an inflation fluid may include inflating the inner chamber and the outer chamber at different pressures in order to drive dissolved gasses out of solution.

Alternatively or additionally, the method may further include periodically changing a pressure of the inflatable balloon in order to provide a pulsatile mechanical pressure to the vessel wall.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
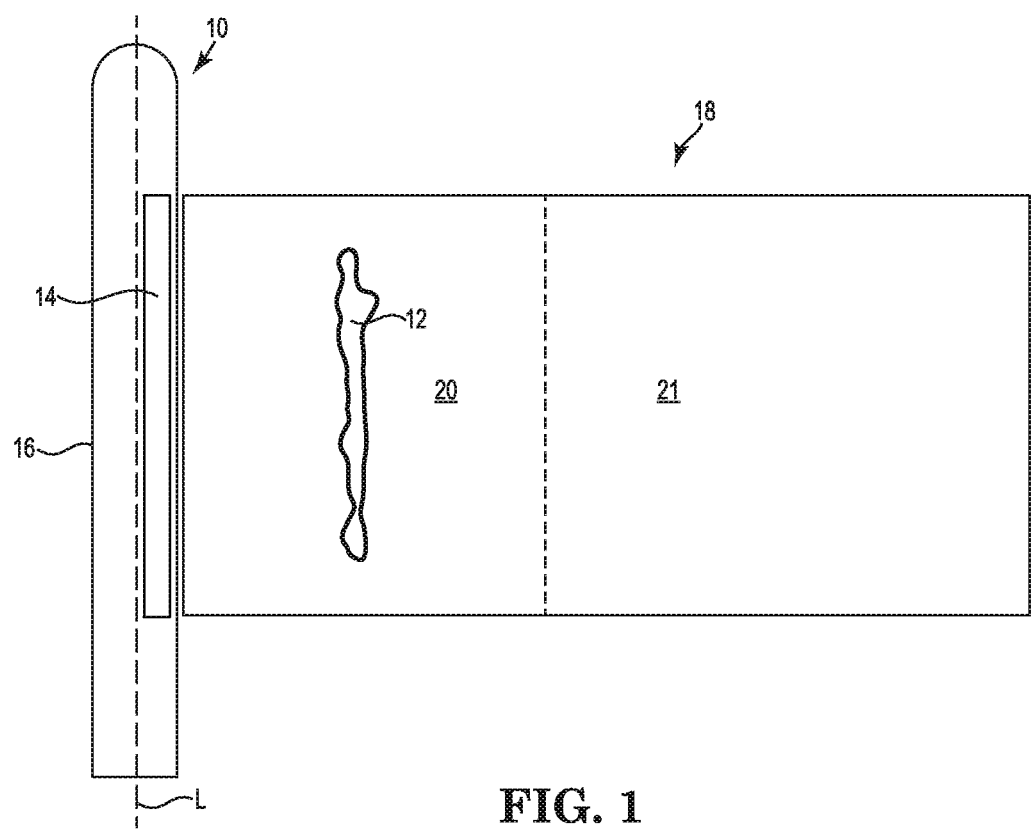
FIG. 1 is a schematic illustration of a near-field ultrasound field created by an ultrasound catheter in accordance with the disclosure.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Many patients suffer from occluded arteries, other blood vessels, and/or occluded ducts or other body lumens which may restrict bodily fluid (e.g. blood, bile, etc.) flow. Occlusions can be partial occlusions that reduce blood flow through the occluded portion of a blood vessel or total occlusions (e.g., chronic total occlusions) that substantially block blood flow through the occluded blood vessel. Revascularization techniques include using a variety of devices to pass through the occlusion to create or enlarge an opening through the occlusion. In some cases, lesions such as calcified lesions may create problems for revascularization techniques, and it may be beneficial to treat the calcified lesions in order to soften them and make them more malleable.

In some cases, for example, ultrasound may be used to treat vascular lesions, such as fibrotic and calcified lesions, at various states of disease progression, ranging from soft plaques to severely calcified lesions. Vascular lesions that may best lend themselves to being treated with ultrasound-based devices include irregular, severely calcified plaques that are located within and adjacent to vessel walls, and lesions that are more or less rigid and thus may be susceptible to being mechanically fatigued to failure. For example, ultrasound-based devices may be used to produce standing wave pressure patterns within the thickness of the lesion, bending moments at the ends of the lesion, and/or resonance along the length of the lesion. In some cases, the high frequency mechanical action of ultrasound may also be effective in treating earlier state vascular lesions, including fibrotic and soft plaques. In some cases, an ultrasound device may apply a treatment of unfocused, near-field ultrasound waves to treat vascular lesions.

An intravascular device such as an ultrasound catheter may be placed within a blood vessel in order to treat a vascular lesion that is within or adjacent to a vessel wall of the blood vessel. FIG. 1 is a schematic view of an ultrasound catheter 10 placed proximate a calcified lesion 12. The ultrasound catheter 10 includes an ultrasound transducer 14 disposed relative to an elongate shaft 16. In some cases, the ultrasound transducer 14 may include a piezoelectric material, which transmits acoustic pressure in response to an applied voltage. The ultrasound transducer 14 may be driven at one or more frequencies in the range of about 20 kilohertz (kHz) to about 50 megahertz (MHz). The ultrasound transducer 14 may be a single ultrasound transducer, or the ultrasound transducer 14 may include a series of ultrasound transducers that may be operated to effectively function as a single ultrasound transducer, providing the desired acoustic pressure over the desired treatment area. The acoustic pressure applied may range from tens of kiloPascals (kPa) to in excess of ten megaPascals (MPa).

As can be seen in the example of FIG. 1, the ultrasound transducer 14 produces an ultrasound field 18 that includes a near field region 20 and a far field region 21. In the near field region 20, dynamic acoustic pressures may be cyclically applied to the calcified lesion 12. As used in this application, the near field region 20 refers to a region in close proximity radially to a surface of the ultrasound transducer 14, for example, the region extending outward from the transducer surface to a radial distance less than or equal to a length of the ultrasound transducer 14, wherein the acoustic pressure waves transmitted by the ultrasound transducer 14 are unfocused and can be controlled to be substantially uniform upon the calcified lesion 12. In some cases, the ultrasound catheter 10 may include additional structure, such as an inflatable balloon as will be discussed with respect to subsequent drawings.

In some cases, for example, the ultrasound transducer 14 may be configured to impart a uniform or substantially uniform acoustic pressure along the length of the calcified lesion 12. In cardiac vessel disease states, vascular lesions may span a length of 10 millimeters (mm) to 25 mm in vessels that are 2 mm to 4 mm in diameter. In peripheral vessel disease states, vascular lesions may span a length of up to 200 mm in vessels up to 12 mm in diameter. Depending on the therapeutic applications, the ultrasound transducer 14 may be configured to impart a uniform or substantially uniform acoustic pressure over a length of about 10 mm to about 60 mm at a radial distance of about 1 mm to about 8 mm as measured from a central axis L extending through the elongate shaft 16. While not illustrated, one can appreciate that multiple ultrasound transducers 14 may be configured upon a catheter to extend the effective therapeutic length, such as up to a length of 200 mm.

To impart a uniform or substantially uniform acoustic pressure in the near field 20, the ultrasound transducer 14 may have a length that is multiple times larger than a diameter of the ultrasound catheter 10. In some cases, the ultrasound transducer 14 may have a length that is at least as long as a length of the calcified lesion 12, in some cases, to generate a uniform or substantially uniform acoustic pressure over a length of about 20 to about 80 mm.

Figure 2:
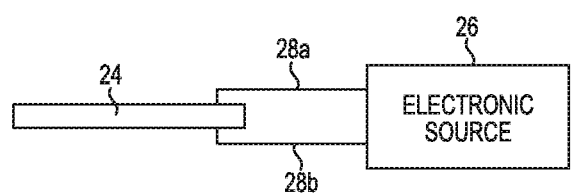
FIG. 2 is a schematic illustration of an ultrasound transducer system in accordance with the disclosure.
Figure 3:
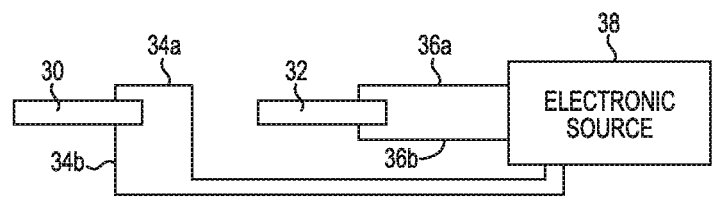
FIG. 3 is a schematic illustration of an ultrasound transducer system in accordance with the disclosure.
Figure 4:
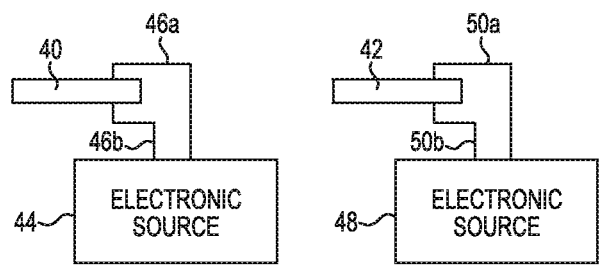
FIG. 4 is a schematic illustration of an ultrasound transducer system in accordance with the disclosure.

In some instances, the ultrasound transducer 14, may be a single ultrasound transducer or a series of ultrasound transducers or transducer elements driven in such a way as to effectively act as a single ultrasound transducer. FIGS. 2-4 provide illustrative but non-limiting examples of how the ultrasound transducer 14 may be controlled. In FIG. 2, a single ultrasound transducer 24 is electrically coupled to an electronic source 26 via wires 28a, 28b. FIG. 3 shows an ultrasound transducer 30 and an ultrasound transducer 32. The ultrasound transducer 30 is electrically coupled to an electronic source 38 via wires 34a, 34b and the ultrasound transducer 32 is electrically coupled to the electronic source 38 via wires 36a, 36b. In this case, the ultrasound transducer 30 and the ultrasound transducer 32 are driven with the same frequency and output from the electronic source 38. FIG. 4 shows an ultrasound transducer 40 and an ultrasound transducer 42. The ultrasound transducer 40 is electrically coupled to an electronic source 44 via wires 46a, 46b. The ultrasound transducer 42 is electrically coupled to an electronic source 48 via wires 50a, 50b. In this case, the ultrasound transducers 40, 42 are independently driven with the electronic sources 44, 48, respectively, and amplitude and phase control may be applied to increase the uniformity of the acoustic pressure imparted to the calcified lesion 12. While FIGS. 3 and 4 each show a pair of ultrasound transducers 30, 32 and 40, 42, it will be appreciated that this is merely illustrative, as any number of distinct ultrasound transducers may be utilized.

Figure 5:
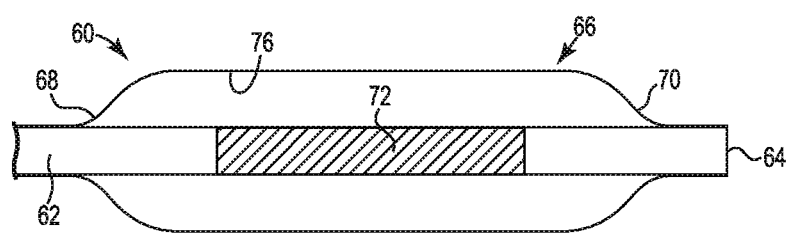
FIG. 5 is a schematic illustration of an ultrasound catheter in accordance with the disclosure.

FIG. 5 is a schematic view of a distal portion of an ultrasound catheter 60 that includes an elongate shaft 62 that terminates at a distal end 64. In some cases, the distal end 64 may include an atraumatic tip, for example. An inflatable balloon 66 is secured relative to the elongate shaft 62. In some cases, as illustrated, the inflatable balloon 66 includes a proximal waist 68 and a distal waist 70, and is secured to the elongate shaft via the proximal waist 68 and the distal waist 70. The inflatable balloon 66 may be formed of any suitable polymeric material, and may for example be compliant or non-compliant, i.e., the inflatable balloon 66 may have an inflated size and shape that is locked in, or the inflatable balloon 66 may have an inflated size and shape that varies upon inflation pressure. An ultrasound transducer 72 may be secured relative to the elongate shaft 62. In some cases, the inflatable balloon 66 may be sized such that the proximal waist 68 is disposed proximal of the ultrasound transducer 72 and the distal waist 70 is disposed distal of the ultrasound transducer 72.

The inflatable balloon 66 may be inflated using any suitable inflation fluid. Examples include water, saline (e.g., 0.9% sodium chloride), and a mixture of saline and a radiopaque contrast agent (e.g., a 50/50 mixture). In some cases, the inflation fluid may be chosen for how acoustic energy transmits through the inflation fluid. It will be appreciated that by selecting a particular fluid with which to inflate the inflatable balloon 66, one is able to control the efficiency of acoustic energy transmission through the fluid and to the calcified lesion 12 (FIG. 1). In one example, the inflation fluid may be chosen to have a specific characteristic acoustic impedance to serve as an acoustic matching between the ultrasound transducer 72 and the vessel wall. In another example, the inflation fluid may be chosen to have a specific characteristic acoustic impedance to serve as an acoustic matching to minimize transmission loss across a wall of the inflatable balloon 66. In another example, the inflation fluid may be chosen to have a specific sound velocity in order to modify the near field behavior of the ultrasound transducer 72.

Figure 6:
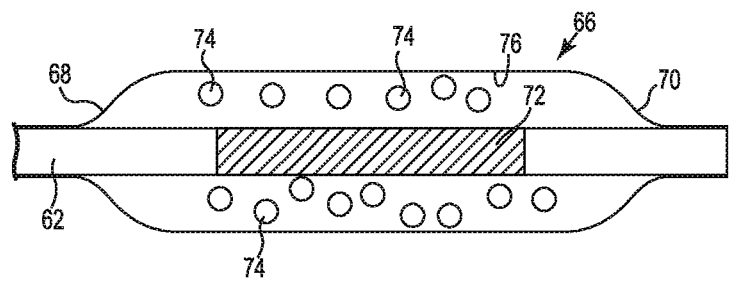
FIG. 6 is a schematic illustration of an ultrasound catheter in accordance with the disclosure.

In some cases, the inflation fluid may include dissolved gas, gas bubbles, stabilized microbubbles, droplets, commercial ultrasound contrast agent, or other cavitation nuclei which may be excited into resonance, collapse and cavitation behavior by the ultrasound transducer 72 to generate or significantly amplify the acoustic pressure waves impinging upon the calcified lesion. As shown for example in FIG. 6, the inflation fluid may include a saline solution with an abundant population of cavitation nuclei 74 in suspension. In some cases, the cavitation nuclei 74 may be configured, chemically or otherwise, to preferentially migrate towards an inner wall 76 of the inflatable balloon 66. The cavitation nuclei 74 in the inflation fluid may, for example, have an average diameter that ranges from about 1 micron to about 2500 microns. In some cases, the size distribution and type of cavitation nuclei 74 may be optimally matched to the sound field frequency and pressure transmitted by the ultrasound transducer 72. In some cases, the size distribution and type of cavitation nuclei 74 may be selected based at least in part upon a collapse pressure and penetration depth selected for a particular treatment target. As an example, 3 micron diameter, air filled microbubbles may be selected as an optimal cavitation nuclei for an ultrasound catheter with an ultrasound transducer 72 operating at 1 megahertz (MHz). The cavitation nuclei 74 may be replenished by injection through the catheter into the inflatable balloon 66, by sonication from the ultrasound transducer 72, as well as by other methods. In some cases, the inner wall 76 of the inflatable balloon 66, a surface of the ultrasound transducer 72, and/or one or more surfaces of the elongate shaft 62, may include a surface treatment such as a hydrophilic or hydrophobic coating or mechanical patterning to localize, trap, collect, or nucleate the cavitation nuclei 74. In some cases, the surface treatments may be selected to drive the cavitation nuclei 74 to locations where they will be most effective in amplifying the pressure waves impinging on the calcified lesion. In other cases, the surface treatment(s) may be selected to drive cavitation nuclei 74 away from a surface of the ultrasound transducer 72.

Figure 8:
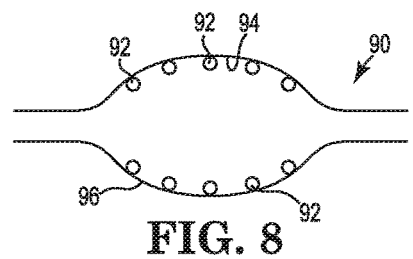
FIG. 8 is a schematic illustration of an inflatable balloon having a mechanical pattern formed on an surface of the inflatable balloon in accordance with the disclosure.
Figure 7:
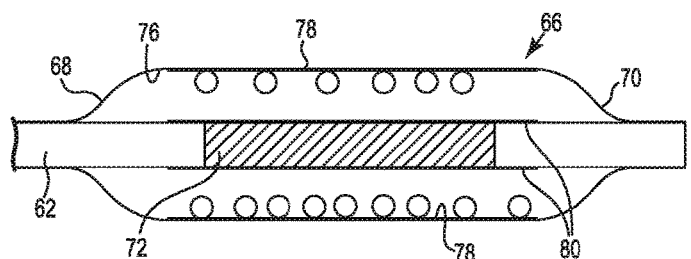
FIG. 7 is a schematic illustration of an ultrasound catheter in accordance with the disclosure.
Figure 9:
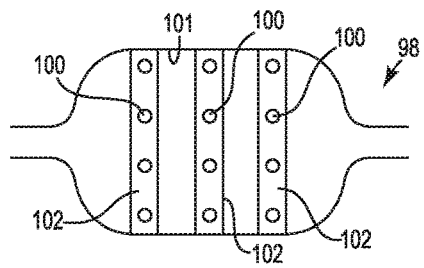
FIG. 9 is a schematic illustration of an inflatable balloon having a mechanical pattern formed on an surface of the inflatable balloon in accordance with the disclosure.
Figure 10:
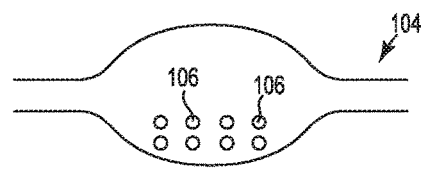
FIG. 10 is a schematic illustration of an inflatable balloon having a mechanical pattern formed on an surface of the inflatable balloon in accordance with the disclosure.

FIGS. 7 through 10 show illustrative but non-limiting examples of surface treatment that may be used. In some cases, as shown for example in FIG. 7, the ultrasound catheter 60 may include a hydrophilic surface treatment 78 on the inner wall 76 of the inflatable balloon 66 and/or a hydrophobic surface treatment 80 on the ultrasound transducer 72 and the elongate shaft 62. Examples of suitable hydrophilic treatments include polyarylene oxides, polyvinylpyrolidones, polyvinylalcohols, hydroxyl alkyl cellulosics. Examples of suitable hydrophobic treatments include silicone based coatings and fluoropolymers. FIGS. 8 through 10 illustrate various patterns that may be applied to localize cavitation nuclei 74. FIG. 8 is a schematic illustration of an inflatable balloon having a mechanical pattern formed on a surface of an inflatable balloon 96. In some cases, as shown for the example in FIG. 8, an ultrasound catheter 90 may include a hydrophilic surface treatment on the inner wall 94 of the inflatable balloon 96. The inflatable balloon 96 includes a series of features that are arranged along the inner wall 94 of the inflatable balloon wall to localize cavitation nuclei 92. In FIG. 9, an inflatable balloon 98 includes a series of features 102 that are arranged circumferentially with uniform axial spacing to localize cavitation nuclei 100 in circular bands along an inner surface 101 of the inflatable balloon 98. In FIG. 10, an inflatable balloon 104 includes a series of features (not illustrated) that are arranged to localize cavitation nuclei 106 uniformly spaced in both radial and axial directions upon the inner surface of the inflatable balloon 104. It will be appreciated that the features described may be mixed and matched, for example, and may be formed in a variety of processes including mechanically removing material from the balloon wall and depositing material on the balloon wall.

Figure 11:
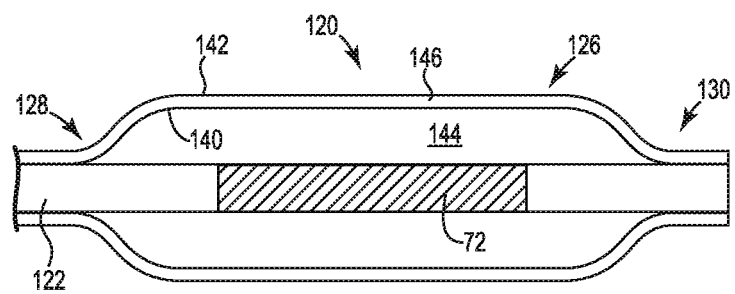
FIG. 11 is a schematic illustration of an ultrasound catheter in accordance with the disclosure.

FIG. 11 is a schematic view of a distal portion of an ultrasound catheter 120 that includes an elongate shaft 122 that terminates at a distal end 124. In some cases, the distal end 124 may be an atraumatic tip, for example. An inflatable balloon 126 is secured relative to the elongate shaft 122. In some cases, the inflatable balloon 126 includes a proximal waist 128 and a distal waist 130, by which the inflatable balloon 126 is secured to the elongate shaft 122. The inflatable balloon 126 may be formed of any suitable polymeric material, and may for example be compliant or non-compliant, i.e., the inflatable balloon 126 may have an inflated size and shape that is locked in, or the inflatable balloon 126 may have an inflated size and shape that varies upon inflation pressure. An ultrasound transducer 72 may be secured relative to the elongate shaft 122. In some cases, the inflatable balloon 126 may be sized such that the proximal waist 128 is disposed proximal of the ultrasound transducer 72 and the distal waist 130 is disposed distal of the ultrasound transducer 72.

In some cases, the inflatable balloon 126 may be a double wall inflatable balloon, having an inner wall 140 and an outer wall 142. An inner chamber 144 is defined within the inner wall 140, and an outer chamber 146 is defined between the inner wall 140 and the outer wall 142. In some cases, the inner wall 140 may be made of a semipermeable material and the outer wall 142 may be made of a non-permeable material. If both the inner chamber 144 and the outer chamber 146 contain a volume of fluid, and a relatively higher pressure is applied to the inner chamber 144 and a relatively lower pressure is applied to the outer chamber 146, the pressure differential may drive gas out of solution in the inner chamber 144 to form gas bubbles or other cavitation nuclei in the outer chamber 146.

In some cases, the outer chamber 146 may contain a volume of gas-saturated fluid, and reducing the pressure in the inner chamber 144 to create a pressure differential may drive gas out of solution in the outer chamber 146. In some cases, the inner chamber 144 may initially contain a volume of gas and the outer chamber 146 may initially contain a volume of fluid (liquid). A relatively higher pressure may be applied to the inner chamber 144 and a relatively lower pressure may be applied to the outer chamber 146. The pressure differential drives gas out of solution in the inner chamber 144 to form nuclei in the outer chamber 146. The gas in the inner chamber 144 may be replaced with a fluid prior to operating the ultrasound transducer 72.

Figure 12:
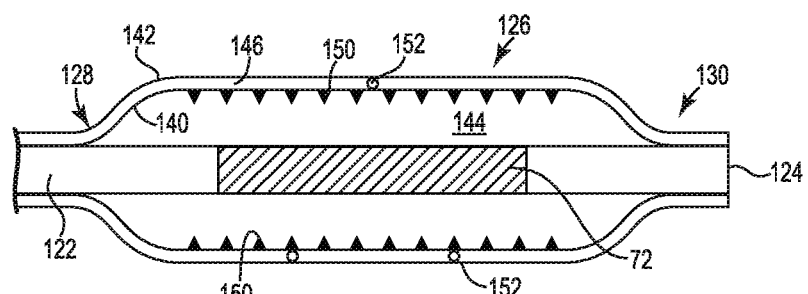
FIG. 12 is a schematic illustration of an ultrasound catheter in accordance with the disclosure.

In some cases, as shown in FIG. 12, the inner wall 140 may include a mechanical patterning 150 such that injection of a gas-saturated fluid into the outer chamber 146 causes bubble generation at the sites of the mechanical patterning 150. In some cases, chemical patterning or chemical surface treatments may be used to influence where and how bubbles nucleate. In some cases, the pressure in the inflatable balloon 126 (or the inflatable balloon 66) may be periodically fluctuated to create a pulsatile mechanical action by the inflatable balloon 126 (or 66).

A variety of polymeric materials may be used in manufacturing the ultrasound catheters 10, 60, 120 described herein. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the polymeric materials may include a liquid crystal polymer (LCP). For example, the mixture can contain up to about 6 percent LCP.

In some cases, the ultrasound catheters 10, 60, 120 may include a lubricious, a hydrophilic, a hydrophobic, a protective, or other type of coating. Hydrophobic coatings such as fluoropolymers provide a dry lubricity which improves device handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The devices described herein may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The scope of the disclosure is, of course, defined in the language in which the appended claims are expressed.

What is claimed is:

1. An ultrasound catheter adapted for placement within a blood vessel having a vessel wall, the ultrasound catheter for treating a calcified lesion within or adjacent the vessel wall, the ultrasound catheter comprising:

an elongate shaft extending from a distal region to a proximal region;

an ultrasound transducer disposed relative to the distal region of the elongate shaft, the ultrasound transducer adapted to impart near-field acoustic pressure waves within the calcified lesion in order to induce fractures in the calcified lesion; and an inflatable balloon disposed about the ultrasound transducer and coupled to the elongate shaft, the inflatable balloon having a collapsed configuration suitable for advancing the ultrasound catheter through a patient's vasculature and an expanded configuration suitable for anchoring the ultrasound catheter in position relative to a treatment site, the inflatable balloon having an inner surface including a mechanical or chemical treatment that localizes, traps, collects or nucleates bubbles;

wherein the inflatable balloon is constructed from a non-permeable material and is configured to be inflated using an inflation fluid, the inflation fluid having cavitation nuclei therein, the inflation fluid being a medium through which the ultrasound transducer transmits acoustic pressure waves.

2. The ultrasound catheter of claim 1, wherein the inflatable balloon comprises a proximal waist and a distal waist, the inflatable balloon secured to the elongate shaft via the proximal waist and the distal waist, with the proximal waist disposed proximal of the ultrasound transducer and the distal waist disposed distal of the ultrasound transducer.

3. The ultrasound catheter of claim 1, wherein the cavitation nuclei can be excited into resonance, collapse or other cavitation behavior to generate or amplify the acoustic pressure waves impinging upon the calcified lesion.

4. The ultrasound catheter of claim 1, wherein the cavitation nuclei having an average diameter of about 1 micron to about 2500 microns.

5. The ultrasound catheter of claim 1, wherein the inflatable balloon has an inner surface, and the inner surface of the balloon includes a hydrophilic treatment.

6. The ultrasound catheter of claim 1, wherein a portion of the ultrasound transducer includes a hydrophobic treatment.

7. The ultrasound catheter of claim 1, wherein the inflatable balloon comprises a single wall balloon.

8. The ultrasound catheter of claim 1, wherein the ultrasound transducer is configured to transmit a substantially uniform acoustic pressure over a length of about 10 millimeters to about 60 millimeters at a radial distance of about 1 millimeters to about 8 millimeters as measured from a longitudinal central axis of the elongate shaft.

9. The ultrasound catheter of claim 1, wherein the inflatable balloon has an inflatable balloon pressure that is periodically fluctuated to create a pulsatile mechanical action.

10. The ultrasound catheter of claim 1, wherein the elongate shaft has a distal end including an atraumatic tip.

11. The ultrasound catheter of claim 1, wherein the ultrasound transducer is configured to cyclically impart near-field dynamic acoustic pressure waves within the calcified lesion in order to induce fractures in the calcified lesion.

12. An ultrasound catheter adapted for placement within a blood vessel having a vessel wall, the ultrasound catheter adapted for causing mechanical fractures in a calcified lesion within or adjacent the vessel wall, the ultrasound device comprising:

an elongate shaft extending from a distal region to a proximal region;

an ultrasound transducer disposed within the distal region of the elongate shaft, the ultrasound transducer adapted to impart unfocused acoustic pressure waves upon the calcified lesion in order to induce fractures in the calcified lesion, the ultrasound transducer having an effective length that is at least twice a distance between the ultrasound transducer and the calcified lesion when the ultrasound catheter is disposed proximate the calcified lesion, the ultrasound transducer including a plurality of individual ultrasound transducers that are each independently electrically driven; and an inflatable balloon that is constructed from a non-permeable material, disposed about the ultrasound transducer, and coupled to the elongate shaft.

13. The ultrasound catheter of claim 12, wherein the inflatable balloon comprises a proximal waist and a distal waist, the inflatable balloon secured to the elongate shaft via the proximal waist and the distal waist, with the proximal waist disposed proximal of the ultrasound transducer and the distal waist disposed distal of the ultrasound transducer.

14. The ultrasound catheter of claim 12, wherein the inflatable balloon is constructed from a non-permeable material.

15. The ultrasound catheter of claim 12, wherein the inflatable balloon has an inner surface that includes a hydrophilic treatment.

16. The ultrasound catheter of claim 12, wherein a portion of the ultrasound transducer includes a hydrophobic treatment.

17. An ultrasound catheter adapted for placement within a blood vessel having a vessel wall, the ultrasound catheter for treating a calcified lesion within or adjacent the vessel wall, the ultrasound catheter comprising:

an elongate shaft extending from a distal region to a proximal region;

an ultrasound transducer disposed relative to the distal region of the elongate shaft, the ultrasound transducer adapted to impart near-field acoustic pressure waves within the calcified lesion in order to induce fractures in the calcified lesion; and an inflatable balloon disposed about the ultrasound transducer and coupled to the elongate shaft, the inflatable balloon having a collapsed configuration suitable for advancing the ultrasound catheter through a patient's vasculature and an expanded configuration suitable for anchoring the ultrasound catheter in position relative to a treatment site, the inflatable balloon having a double wall forming an inner chamber proximate the ultrasound transducer and an outer chamber surrounding the inner chamber;

wherein the inflatable balloon is constructed from a non-permeable material and is configured to be inflated using an inflation fluid, the inflation fluid having cavitation nuclei therein, the inflation fluid including a medium through which the ultrasound transducer transmits acoustic pressure waves.

18. The ultrasound catheter of claim 17, wherein the inner chamber and the outer chamber are configured to be inflated at different pressures.

19. The ultrasound catheter of claim 17, wherein the inner chamber is formed from a semipermeable material and the outer chamber is formed from a non-permeable material.

20. The ultrasound catheter of claim 17, wherein the double wall comprises an inner wall that is formed of a semipermeable material and an outer wall that is formed of a non-permeable material.

* * * * *